United States Patent
Ferguson et al.

(10) Patent No.: US 7,332,305 B2
(45) Date of Patent: Feb. 19, 2008

(54) GENETIC POLYMORPHISM IN THE ZF9 GENE LINKED TO INAPPROPRIATE SCARRING OR FIBROSIS

(75) Inventors: Mark William James Ferguson, Derbyshire (GB); William Ernest Royce Ollier, Cheshire (GB); Ardeshir Bayat, Manchester (GB)

(73) Assignee: Renovo Limited, Manchester (GB)

( * ) Notice: Subject to any disclaimer, the term of this patent is extended or adjusted under 35 U.S.C. 154(b) by 351 days.

(21) Appl. No.: 10/469,609

(22) PCT Filed: Mar. 1, 2002

(86) PCT No.: PCT/GB02/00847

§ 371 (c)(1), (2), (4) Date: Feb. 23, 2004

(87) PCT Pub. No.: WO02/070745

PCT Pub. Date: Sep. 12, 2002

(65) Prior Publication Data

US 2004/0161761 A1 Aug. 19, 2004

(30) Foreign Application Priority Data

Mar. 2, 2001 (GB) .................. 0105330.5

(51) Int. Cl.
*C12P 19/34* (2006.01)

(52) U.S. Cl. .................................... 435/91.2

(58) Field of Classification Search .................... None
See application file for complete search history.

(56) References Cited

U.S. PATENT DOCUMENTS 5,422,242 A * 6/1995 Young ........................ 435/6

FOREIGN PATENT DOCUMENTS

| WO | WO 98/58063 | 12/1998 |
| WO | WO 99/55912 | 11/1999 |
| WO | WO 00/50869 | 8/2000 |
| WO | WO 01/48245 | 7/2001 |
| WO | WO 02/12894 | 2/2002 |
| WO | WO 0212894 A1 * | 2/2002 |

OTHER PUBLICATIONS

Ratziu et al., Zf9, a Kruppel-Like Transcription Factor Up-Regulated in vivo during Early Hepatic Fibrosis, Proc. Nat. Acad. Sci., Aug. 1998, vol. 95, No. 16, pp. 9500-9505.*
Koritschoner, N et al., "A Novel Human Zinc Finger Protein that Interacts with the Core Promoter Element of a TATA Box-less Gene," Journal of Biological Chemistry, Apr. 1997, vol. 272, No. 14, 9573-9580.*
Buck et al., "Design Strategies and Performance of Custom DNA Sequencing Primers," Biotechniques, Sep. 1999, vol. 27, No. 3, pp. 528-536.*
Dias Neto et al, "Shotgun sequencing of the human transcriptome with ORF expressed sequence tags", Proc. Natl. Acad. Sci. USA 97(7):3491-3496 (2000).
Ratziu et al, "Zf9, a Kruppel-like transcription fact up-regulated in vivo during early hepatic fibrosis", Proc. Natl. Acad. Sci. USA 95:9500-9505 (1998).
Ratziu et al, "A Key Role for ZF9 in Hepatic Fibrosis Via Its Transcriptional Activation of TGFβ1 and Types I and II TGFβ Receptor Genes in Rat Stellate Cells", p. 227(1997)—XP008015024.
Database NCBI-SNP 'Online! NCBI, "dbSNP build of first appearance: 63", (1999) Database accession No. rs17731—XP002235529.
Burge, Peter, "Genetics of Dupuytren's Disease", Hand Clinics 15(1):63-71 (1999).

* cited by examiner

*Primary Examiner*—Kenneth R. Horlick
*Assistant Examiner*—Molly E. Baughman
(74) *Attorney, Agent, or Firm*—Nixon & Vanderhye P.C.

(57) ABSTRACT

The present invention relates to an in vitro method for diagnosing or detecting a predisposition to a condition at least partially characterised by inappropriate fibrosis or scarring (e.g. Dupuytren's Disease). The method comprises examining the ZF9 gene, and regulatory elements thereof, derived from a subject of interest to detect the presence of a genetic poylmorphism or mutation in said gene which is linked with the condition.

8 Claims, 2 Drawing Sheets

Figure 1:
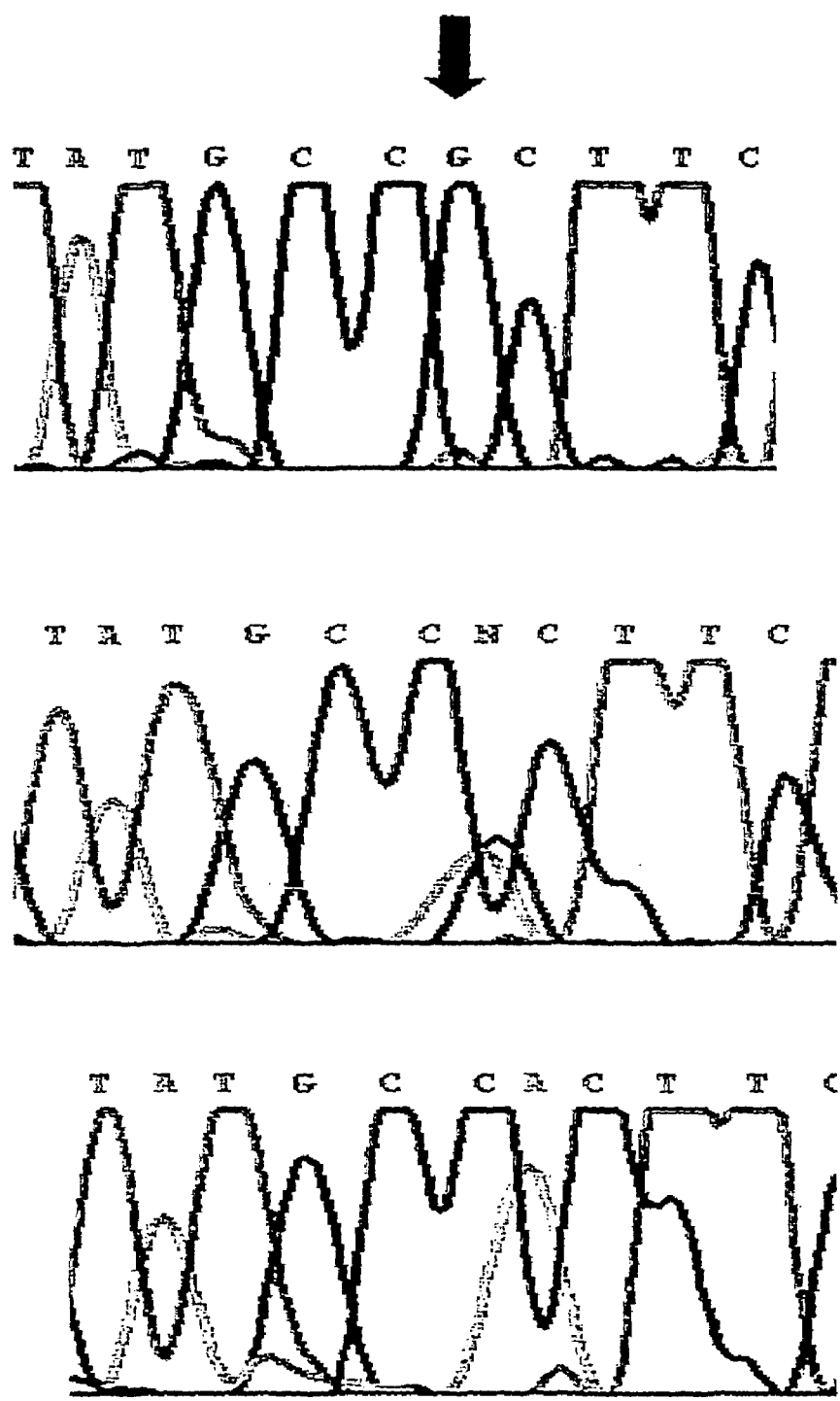

GENETIC POLYMORPHISM IN THE ZF9 GENE LINKED TO INAPPROPRIATE SCARRING OR FIBROSIS

This application is the US national phase of international application PCT/GB02/00847 filed 01 Mar. 2002, which designated the US.

The present invention relates to methods for the genetic testing of samples to determine the presence of polymorphisms in the Zf9 gene that are linked to a genetic predisposition to develop conditions at least partially characterised by inappropriate scarring or fibrosis.

A scar is an abnormal morphological structure resulting from a previous injury or wound (e.g. an incision, excision or trauma). Scars are composed of a connective tissue which is predominately a matrix of collagen types 1 and 3 and fibronectin. The scar may consist of collagen fibres in an abnormal organisation (as seen in normal scars of the skin) or it may be, an abnormal accumulation of connective tissue (as seen in scars of the central nervous system or pathological scarring of the skin).

Scarring is a usual consequence of the healing process in most adult animal and human tissues. In the skin scars may be depressed below the surface or elevated above the surface of the skin. Hypertrophic scars are a more severe form of scarring that can arise in certain conditions or certain individuals. Hypertrophic scars are elevated above the normal surface of the skin and contain excessive collagen arranged in an abnormal pattern. A keloid is a form of pathological scarring which is not only elevated above the surface of the skin but also extends beyond the boundaries of the original injury. In a keloid there is excessive connective tissue which is organised in an abnormal fashion predominantly in whorls of collagenous tissue.

There are believed to be genetic predispositions to forming inappropriate, and particularly pathological, scarring (e.g. hypertrophic scars and keloids). For instance, Africo-Carribean and Mongoloid races are particularly prone to developing keloid scars.

There are numerous medical situations where scar formation represents a problem. Examples of such situations are scars of the skin where excessive scarring may be detrimental to tissue function and particularly when scar contracture occurs (for instance skin burns and wounds that impair flexibility of a joint). The reduction of scarring to the skin when cosmetic considerations are important is also highly desirable. In the skin, hypertrophic or keloid scars particularly in Africo-Caribbean and Mongoloid races) can cause functional and cosmetic impairment and there is a need to prevent their occurrence. Scarring resulting from skin grafts in both donor sites and from the application of artificial skin can also be problematic and need to be minimised or prevented. Given the importance of scarring in such situations, it will be appreciated that there is a need to be able to test a subject to investigate whether or not they will be susceptible to developing inappropriate scarring.

As well as scars of the skin, internal scarring or fibrosis can be highly detrimental and specific examples include:

(i) Within the central nervous system, glial scarring can prevent neuronal reconnection (e.g. following neuro-surgery or penetrating injuries of the brain).

(ii) Scarring in the eye can be detrimental. In the cornea, scarring can result in abnormal opacity and lead to problems with vision or even blindness. In the retina, scarring can cause buckling or retinal detachment and consequently blindness. Scarring following wound healing in operations to relieve pressure in glaucoma (e.g. glaucoma filtration surgery) results in the failure of the surgery whereby the aqueous humour fails to drain and hence the glaucoma returns.

(iii) Scarring in the heart (e.g. following surgery or myocardial infarction) can give rise to abnormal cardiac function.

(iv) Operations involving the abdomen or pelvis, often result in adhesion between viscera. For instance, adhesions between elements of the gut and the body wall may form and cause twisting in the bowel loop leading to ischaemia, gangrene and the necessity for emergency treatment (untreated they may even be fatal). Likewise, trauma or incisions to the guts can lead to scarring and scar contracture to strictures which cause occlusion of the lumen of the guts which again can be life threatening.

(v) Scarring in the pelvis in the region of the fallopian tubes can lead to infertility.

(vi) Scarring following injury to muscles can result in abnormal contraction and hence poor muscular function.

(vii) Scarring or fibrosis following injury to tendons and ligaments can result in serious loss of function.

Related to the above is the fact that there are a number of medical conditions known as fibrotic disorders in which the development of excessive fibrotic tissue leads to pathological derangement and malfunctioning of tissue. Fibrotic disorders are characterised by the accumulation of fibrous tissue (predominately collagens) in an abnormal fashion within the tissue. Accumulation of such fibrous tissues may result from a variety of disease processes. These diseases do not necessarily have to be caused by surgery, traumatic injury or wounding. Fibrotic disorders are usually chronic. Examples of fibrotic disorders include cirrhosis of the liver, liver fibrosis, glomerulonephritis, pulmonary fibrosis, cystic fibrosis, scleroderma, myocardial fibrosis, fibrosis following myocardial infarction, central nervous system fibrosis following a stroke or neuro-degenerative disorders (e.g. Alzheimer's Disease), proliferative vitreoretinopathy (PVR) and arthritis.

As is the case for scarring, it is believed that their is a genetic influence on the development of many fibrotic disorders or the severity thereof. In some instances, the genetic influence may be directly responsible for the development of the disorder whereas for other fibrotic disorders there may be a genetic factor that influences fibrotic development which is secondary to the primary cause of the disorder (e.g. in cystic fibrosis).

One example of a disorder that involves fibrosis, and is also believed to be influenced by genetics, is Dupuytren's disease (DD).

DD is a nodular palmar fibromatosis causing progressive and permanent contracture of the digits. DD is often familial and is common in individuals of Northern European extraction. In excess of 25% of males of Celtic races over 60 years of age have evidence of DD and it is considered to be one of the most common heritable disorders of connective tissue in Caucasians.

Autosomal dominance with variable penetrance has been proposed as the likely mode of inheritance for DD. However no single gene has so far been identified in the literature as being responsible for the condition. Furthermore it is unclear whether DD is a complex oligogenic condition or a simple monogenic mendelian disorder. Accordingly the identification of susceptible genetic loci would provide an ideal approach to unravelling the hereditary component of this common disease and would also be valuable in the subsequent development of treatment and management strategies for DD.

It will be appreciated from the above that there is a need to be able to assess individuals for a susceptibility for developing conditions at least partially characterised by inappropriate scarring or fibrosis and also to assess the prognosis for an individual suffering from such a condition. One way in which this may be approached is the identification of polymorphisms or mutations in a gene that may be associated with a particular medical condition. Once identified, such polymorphisms can provide useful information to physicians who need to manage, treat or establish a susceptibility to developing a condition. One way in which the information may be used is in the development of a genetic test.

Genetic testing may be defined as the analytical testing of a patient's nucleic acid to determine if the DNA of a patient contains mutations (or polymorphisms) that either cause or increase susceptibility to a condition or are in association with the gene causing the condition and are thus potentially indicative of a predisposition to that condition.

The early detection of a predisposition to a condition presents the best opportunity for medical intervention. Early genetic identification of risk may improve the prognosis for a patient through early intervention before clinical symptoms manifest.

In cases where patients with similar symptoms are treated with variable success with the same therapeutics, genetic testing may differentiate patients with a genetic rather than developmental basis for their symptoms, thus leading to the potential need for different approaches to therapy.

It is an aim of the present invention to provide methods for genetic screening to indicate a risk or predisposition to conditions at least partially characterised by inappropriate fibrosis or scarring.

According to a first aspect of the present invention there is provided an in vitro method for diagnosing or detecting a predisposition to a condition at least partially characterised by inappropriate fibrosis or scarring, the method comprising examining the ZF9 gene, and regulatory elements thereof, derived from a subject of interest to detect the presence of a genetic polymorphism or mutation.

By "polymorphism" we mean a region of a gene, or regulating elements thereof, where the nucleotide base sequence may vary between individuals. There is often a predominant genotype which represents the usual form, or wild type, of a gene with subsets of a population having a polymorphism which confers a different genotype. Certain polymorphisms can be prevalent in individuals of particular ethnic backgrounds, or from specific geographical areas. A polymorphism may not affect function of the gene; may lead to differences in the function of the gene; may produce an inactive gene product; or may modulate the production of the gene product.

By "mutation" we mean a region of a gene, or regulating elements thereof, where the nucleotide base sequence may vary from the wild type. The mutation may for example comprise a base substitution, deletion or addition. Certain mutant forms of the gene can be prevalent in individuals of particular ethnic backgrounds, or from specific geographical areas. A mutation may not affect function of the gene; may lead to differences in the function of the gene; may produce an inactive gene product; or may modulate the production of the gene product.

By "gene" we mean all coding sequences between the start and stop codon of the Zf9 gene (including introns and exons).

By "regulatory elements" we mean the DNA that is 5' and 3' of the gene and which is involved in regulating gene transcription. For instance, transcription factor binding sequences, the TATA box, the 5' promoter and 5' and 3' untranslated regions (UTRs).

The method according to the first aspect of the invention allows an investigator to identify a subject with a genetic polymorphism or mutation in the ZF9 gene or its regulatory elements to determine those subjects who have, or are more at risk of developing, a condition at least partially characterised by inappropriate fibrosis or scarring. This allows for appropriate action to be taken to prevent or lessen the likelihood of onset of the condition or to allow appropriate treatment thereof. The method is also useful for establishing a prognosis for a subject that has already been diagnosed as suffering form a particular condition.

The transcription factor Zf9 is one of a multitude of biological molecules that is implicated in the pathophysiological processes that lead to the development of a scar or fibrotic tissue. The gene for Zf9 has been mapped to a locus on human chromosome 10p15. The sequence of full-length human (and rat) cDNAs has been identified by Ratziu et al. (Proc. Nat. Acad. Sci 95: 9500-9505, 1998) and the gene sequence of Zf9 is publicly available as Gene Bank Accession No. AB017493.

Zf9 is also known as Core Promoter Element-Binding Protein (COPEB or CPBP); B Cell-derived Protooncogene 1 (BCD1); GC-Rich Sites Binding Factor (GBF); and Kmeppel-like Factor 6 (KLF6).

The inventors performed experiments to screen the Zf9 gene and its regulatory elements for polymorphisms and mutations which may be associated with a condition at least partially characterised by inappropriate fibrosis or scarring. Having established such an association the inventors have established that DNA taken from a subject may be analysed to help establish a diagnosis of the condition or to establish whether or not a subject is predisposed to develop such a condition.

The condition may be a form of pathological scarring of the skin (e.g. hypertrophic scarring or keloids) or an internal scar or fibrosis as mentioned above. Alternatively the condition may be a fibrotic disease or disorder also as mentioned above. Other conditions that may be diagnosed or detected according to the method of the invention include fibrotic disorders of the skin such as:

Sclerodemia
Systemic sclerosis
Crest Syndrome
Tuberous sclerosis with skin patches
Familial cutaneous collagenoma
Metabolic and immunologic disorders of the skin (porphyria cutanea tarda, chronic graft versus host disease)
Eosinophilic facsitis
Discoid lupus erythematosus, Dermatomyositis
Mixed connective tissue disease
Drug-induced skin fibrosis—bleomysin, PVC, silicates
Peyronies
Oral submucous fibrosis
Fibrosis induced following dietary and environmental exposures.

Fibrotic disorders of other organs may also be detected or diagnosed. These include:

Pulmonary/cardiac fibrosis
Liver fibrosis/cirrhosis
Renal fibrosis
GI tract fibrosis
Drug induced fibrosis (e.g. post organ transplantation)
Central and peripheral nervous system fibrosis
Vascular system (veins and arteries) fibrosis Male & female genitourinary tract fibrosis Gynaecological (fallopian tube fibrosis, uterine fibromas)

The method of the first aspect of the invention is particularly suited for diagnosing or detecting a predisposition to Dupuytren's Disease.

The Zf9 gene to be examined is preferably derived from a human subject. However it will be appreciated that DNA derived from animal subjects of vetinary interest may also be tested according to the method of the invention.

Preferred polymorphisms and mutations which may be detected according to the first aspect of the invention are located in the untranslated DNA 3' of the Zf9 coding sequence. A most preferred polymorphism is located at position 1140 of Gene Bank Accession No. AB017493 (NCBI Assay Id (ss#) 20354; and Reference SNP Id (rs#) 17731) and is referred to herein as "the 1140 polymorphism".

ments may be visualised on gels and the polymorphism or mutant identified based upon the number and size (i.e. distance moved on the gel) of the fragments from a DNA sample derived from a subject.

Preferably the DNA comprising the Zf9 gene and/or regulatory elements thereof is amplified prior to detection of the polymorphism This amplification is preferably by means of the polymerase chain reaction (PCR). For instance a preferred method according to the invention known as the PCR-restriction fragment length polymorphism method (PCR-RFLP) is described in more detail in Example 1 and involves PCR amplification of DNA containing the polymorphism prior to RED and subsequent analysis.

PCR primers need to be designed such that they are suitable for amplifying a region around the relevant polymorphism. Suitable primers for amplifying the 1140 polymorphism are listed below as SEQ ID No. 3 and SEQ ID No. 4.

```
Forward primer:   5' GTCCAGGGTC ACCCACATAC 3'   (SEQ ID No. 3)

Reverse primer:   5' GTTCTGCACC CTACCCAGTT 3'   (SEQ ID No. 4)
```

This 1140 polymorphism represents a point mutation of a Guanosine nucleotide (G) to an Adenosine nucleotide (A). Genotypes AA, AG and GG were identified for this polymorphism.

The point mutation is located 1022 bases from the start of the coding sequence of the Zf9 gene and is found in the 3' untranslated region. The two allelic forms have the following base sequence:

For some polymorphisms or mutations neither the wild type nor the mutant allele abolishes or introduces a restriction enzyme site. When this is the case, a restriction enzyme site may be introduced by specifically designing PCR primers that introduce restriction sites into the amplified product. The introduced enzyme site allows differentiation between polymorphic alleles and wild type by size analysis. For

```
The "G" form:
gtccagggtcacccacataccatgcaccacgggtgctatgcc[G]cttcttacagg    (Seq ID No. 1)

acctttttagccctcaaaagaccttccaaggagaggccctggaggcaactgggtag ggtgcagaaac

The "A" form:
gtccagggtcacccacataccatgcaccacgggtgctatgcc[A]cttcttacagga   (Seq ID No. 2)

ccttttagccctcaaaagaccttccaaggagaggccctggaggcaactgggtaggg tgcagaaac
```

Initial experiments established that the GG and AG genotype is significantly over-represented in subjects with Dupuytren's Disease (DD) whereas a higher proportion of control subjects were of an AA genotype.

Further work has established that subjects with other fibrotic disorders (e.g. scleroderma or renal fibrosis) and subjects liable to develop severe/pathological scarring (e.g. keloids) also have a high frequency of the G allelle. Therefore the polymorphism may be examined according to the method of the invention for diagnosing or detecting a predisposition to a variety of conditions at least partially characterised by inappropriate fibrosis or scarring.

Various techniques may be used to detect polymorphisms or mutations according to the method of the invention.

A preferred technique involves Restriction Enzyme Digestion (RED) and is based upon the fact that polymorphisms can lead to the production of different sized DNA fragments following treatment with a restriction enzyme (because of the introduction or deletion of a restriction site by the mutation causing the polymorphism). These fragexample if the restriction products of the amplified product are analysed by gel electrophoresis (agarose or polyacrylamide gel, for example) the alleles with the introduced restriction enzyme site will produce an extra band on the gel.

Other techniques that may be used to detect polymorphisms or mutations according to the present invention include:

(1) Direct sequencing of the polymorphic region of interest (e.g. using commercially available kits such as the Cy5™ Thermo Sequenase™ dye terminator kit—Amersham Pharmacia Biotech);

(2) Sequence Specific Oligonucleotide Hybridization (SSO) (involving dot or slot blotting of amplified DNA molecules comprising the polymorphic region; hybridisation with labelled probes which are designed to be specific for each polymorphic variant; and detection of said labels);

(3) Heteroduplex and single-stranded conformation polymorphism (SSCP) Analysis (involving analysis of electrophoresis band patterns of denatured amplified DNA molecules comprising the polymorphic region);

(4) Sequence Specific Priming (SSP) [also described as Amplification Refractory Mutation System (ARMS)];

(5) Mutation Scanning [e.g. using the PASSPORTS™ Mutation Scanning Kit (Amersham Pharmacia Biotech)];

(6) Chemical Cleavage of Mismatch Analysis;

(7) Non-isotopic RNase Cleavage Assay (Ambion Ltd.);

(8) Enzyme Mismatch Cleavage Assay; and (9) Single Nucleotide Extension Assay.

The method according to the first aspect of the invention is particularly suitable for being carried out on genomic DNA, particularly on isolated genomic DNA. Such genornic DNA may be isolated from blood or tissue samples (e.g. hair, oral buccal swabs, nail or skin) or from other suitable sources using conventional methods. Preferably the DNA is isolated from whole blood or granulocytes.

A prediction or diagnosis based upon the method according to the present invention depends upon an association being made between a particular condition and the specific polymorphism or mutant in question. Such associations were established by the inventors by performing further experiments and making statistical analyses (e.g. see the Example). Association between the 1140 polymorphism are discussed above and in the Examples. Provision of data based upon association analyis enables a clinician to interpret the significance of genotypes identified by sequencing DNA according to the method of the invention. The clinician may then make a judgment regarding the likelihood of a patient developing, or having, a particular disease or disorder. Such knowledge is important in the clinical management of specific conditions associated with inappropriate scarring or fibrosis. It will be appreciated that data relating to the association of a particular genotype with a condition may be provided to a user of the method according to the invention (e.g. a technician or clinician) by incorporating a data sheet as part of a kit (see below).

Genetic testing may be carried out either pre-natally, peri-natally or post-natally when it is desired to test whether or not a neonate or child is likely to have inherited a predisposition to develop a condition at least partially characterised by inappropriate fibrosis or scarring. This is particularly useful when there is believed to be a family history of developing the condition.

The test is particularly useful for testing subjects pre-operatively. The results of such a test are useful for establishing whether or not there could be healing complications for the subject undergoing surgery (e.g. hypertrophic scarring, keloids or internal fibrosis/scarring).

The test is also useful before a therapeutic regimen is established for treating a condition characterised by inappropriate scarring or fibrosis. The results of the test according to the invention may be used by a clinician to help in the selection of medicaments used and the dosage thereof.

It is most preferred that the method of the invention is used to test subjects with a family history of developing a condition at least partially characterised by inappropriate scarring or fibrosis.

The various elements required for a technician to perform the method of the first aspect of the invention may be incorporated in to a kit. Thus according to a second aspect of the present invention there is provided a kit comprising:

A) PCR primers for amplifying genetic polymorphisms in the ZF9 gene and regulatory elements thereof that are linked to a condition characterised by inappropriate scaring or fibrosis; and B) Control DNA samples of known genotype for each polymorphism.

It is preferred that the kit comprises primers specific for a target sequence of sample DNA known to contain a polymorphism of interest For instance, suitable PCR primers for a kit for genotyping the 1140 polymorphism are the primers of SEQ ID No. 3 and SEQ ID No. 4.

The kit may farther comprise:

C) a suitable restriction enzyme for generating fragments of the DNA sample;

D) a data card outlining linkage between a particular polymorphism and a disease;

E) protocols for PCR amplification, restriction enzyme digestion of PCR products and agarose gel electrophoresis of DNA fragments;

F) relevant buffers.

Buffers provided with the Kit may be in liquid form and preferably provided as pre-measured aliquots. Alternatively the buffers may be in concentrated (or even powder form) for diluting.

The Kit may further comprise suitable reaction vessels, centrifuge tubes etc.

A multitude of biological molecules are involved in the fibrotic or scarring process and it would be expected that many different factors lead to the development of a scar or fibrosis. The growth factor TGF-β1 is an example of a biological molecule which has been implicated as a major factor in the development of scars and fibrotic tissues. The TGF-β1 gene is known to be polyniorphic and several polymorphisms of the TGF-β1 gene have been reported in the literature. The inventors explored the hypothesis that there is an association between four known TGF-β1 polymorphisms and the fibrotic condition Dupuytren's disease. TGF-β1 genotyping was performed in Caucasian individuals with DD and compared with a control Caucasian population These studies established that there was a negative association between the Caucasian controls and Dupuytren's disease cases for the TGF-β1 polymorphisms. The fact that polymorphisms in a fibrotic growth factor such as TGF-β1 did not exhibit any association with a condition characterised by inappropriate scarring or fibrosis, illustrates how surprising the inventors' discovery was that the polymorphisms in the gene for Zf9 showed such significant association.

Figure 2:
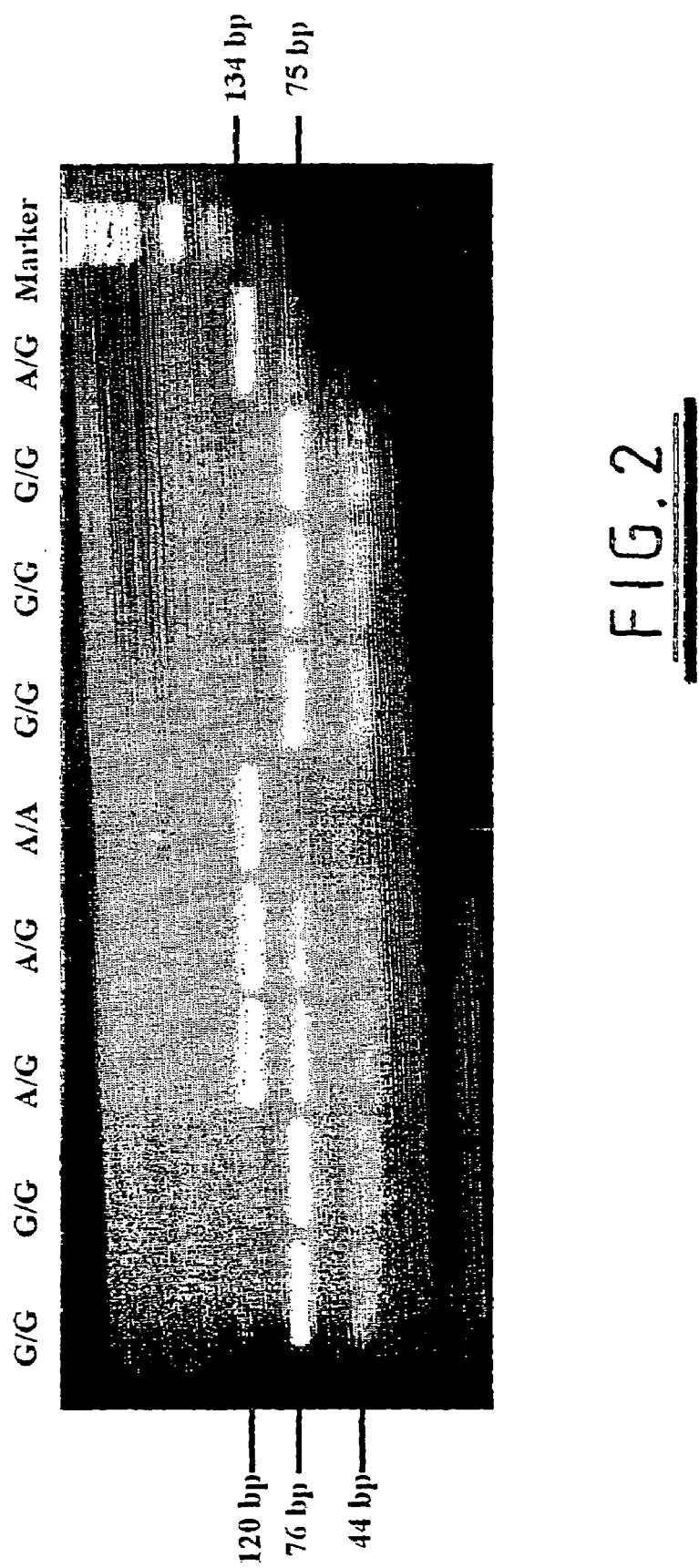

The invention will be further described, by way of example only, with reference to the accompanying drawing, in which:

FIG. 1 is an electropherogram illustrating the polymorphism at position 1140 Gene Accession No. AB017493; and FIG. 2 is a photograph of a gel illustrating the difference in size of amplified DNA fragments corresponding to the genotypes GG, AG and AA in Example 1

EXAMPLE 1

Linkage Analysis of a ZF9 Polymorphism

Samples were taken from a group of patients with Dupuytren's Disease (DD) and a control group to investigate the correlation between a Zf9 polymorphism and the condition.

1.1. Patients & Methods 1.1.1 Patients

Dupuytren's patients (n=138) were entered into the study (119 men and 19 women). The age range was between 37 to 90 years with a mean age of 55.8 years. Cases were all unrelated Caucasians from the Northwest region of England, U.K. Dupuytren's cases were identified through operative record clinical codes from the South Manchester University Hospital Trust and Wrightington Hospital in the North West region. All patients were seen by a medically qualified person who took a full medical history using a proforma and examined both hands of each case. All cases had confirmed diagnosis of Dupuytren's disease pre-operatively with the presence of characteristic dupuytren's nodules in the palm of the hand and/or digits with or without contracture of either the MCPJ or the PIPJ.

A control group (n=161) comprised ethnically matched healthy Caucasian men and women and was selected from general practice registers.

The local and hospital ethical committees had given approval for the study protocol and profomias. Written consent was obtained from all individuals.

1.1.2 DNA Extraction Method

Blood samples were collected from subjects using standard techniques (15 ml of venous blood were collected).

DNA was extracted from peripheral blood cells using a commercially available DNA extraction kit (Qiagen,UK). DNA concentrations were measured and diluted in buffer to 100 ng/µl using sterile, Qiagen buffer.

1.1.3 Genotyping Method

Zf9 genotyping was carried out using the polymerase chain reaction-restriction fragment length polymorphism (PCR-RFLP) method.

The polymorphism chosen for the study was found to be in the 3' untranslated region of the ZF9 gene and corresponded to the 1140 polymorphism described above (NCBI Assay Id(ss#): 20354 Reference SNP Id(rs#): 17731).

PCRs were carried out in 96 well microlitre plates. Each PCR consisted of 1 µl of DNA (100 ng/µl ), 2.5 µl of x1 NH$_4$ buffer (Bioline), 2.5 µl of each 2 mM d'NTP (Behring), 0.1 µl of 0.1 unit Taq polyrnerase (Bioline), 6 µl of Betaine, 0.75 µl MgCl$_2$, 0.1 µl each of 2.5 pmol forward and reverse primer of Sequence I.D. No 2 and 3 respectively and made up to 25 µl reaction mix with autoclaved, distilled water. The sequences of the primers used are given below:

```
Forward    GTCCAGGGTC ACCCACATAC;   (Seq I.D. No. 3)
Primer:

and

Backward   GTTCTGCACC CTACCCAGTT    (Seq I.D. No. 4)
Primer:
```

PCR was carried out under the following conditions: 2 minutes of denaturation at 95° C.; followed by 35 cycles of further denaturation of 45 seconds at 95° C.; then 1 minute at either annealing temperature (as listed in table 1), and 45 seconds of extension at 72° C.; a final elongation step of 5 minutes at 72° C. was included.

The PCR-RFLP conditions was as follows: Amplified DNA (5 µl) was digested with the appropriate enzyme (0.8 µl) including buffer (1 µl) and made up to a 10 µl reaction mixture using distilled water. Digestion was carried out overnight in a Hybaid Omnigene thermal cycler. The enzyme used was Aci I (recognition sequence ccgc). Enzyme was purchased from the New England Biolabs. The digested products were fractionated in 4% polyacrylamide gels and visualised by ethidium bromide and ultraviolet light using standard procedures.

1.1.4 Statistical Analysis

Association with DD was investigated by comparing the distribution of its allele frequencies between DD patients and controls using a single global Pearson's chi-squared test. STATA 6 statistical data analysis programme was used to calculate p values and odds ratios.

1.2 Results

The results of an electropherogram of the region surrounding the 1140 region of Genbank Accession No. AB017493 are presented in FIG. 1 and confirm the existence of the G/A polymorphism.

Having confirmed the existence of the polymorphism, DNA Fragments generated according to method 1.1.3 were run on polyacrylarnide gels as specified. FIG. 2 illustrates that different genotypes generated DNA fragments of a unique size which could easily be differentiated by reading the gel. Accordingly gels were generated for each individual in both the DD group and control group and statistical analysis made of any linkage between genotype and health status.

Statistical analysis of the genotyped samples are provided in Table 1. These data illustrate that the GG and AG genotype is significantly over-represented in subjects with Dupuytren's Disease (DD) whereas a higher proportion of control subjects were of an AA genotype.

Accordingly a linkage between the GG and AG genotypes of the 1140 polymorphism in the 3' untranslated region of the Zf9 gene and DD was established. It will be appreciated that such a linkage will also exist with other conditions characterised by inappropriate scarring or fibrosis.

Table 1: Zf9 genotype & allele frequencies

|  | DD Cases (n = 138) | CONTROL (n = 161) |
|---|---|---|
| Allele frequency | | |
| 1 (A) | 84 (30%) | 128 (40%) |
| 2 (G) | 192 (70%) | 194 (60%) |
| Genotype frequency | | |
| 1 (A/A) | 13 (9%) | 23 (14%) |
| 2 (A/G) | 58 (42%) | 82 (51%) |
| 3 (G/G) | 67 (49%) | 56 (35%) | p-value = 0.046

EXAMPLE 2

Having established a correlation between a condition characterised by inappropriate scarring or fibrosis and a genotype conferred by the 1140 polymorphism for ZF9, the methodology of Example 1 was repeated to screen subjects according to the method of the first aspect of the invention to establish the genotype of the subject.

The results of the genetic test could then be used by a clinician to provide medical advice to the individuals. For instance, asymptomatic individuals found to have the G allele may be advised that they were at increased risk of developing a condition characterised by inappropriate scarring or fibrosis. If appropriate, such individuals could be advised to make life style changes and/or receive prophylactic treatment. Individuals having the G allele, who are already suffering from a condition characterised by inappropriate scarring or fibrosis, may be advised to adjust their medication or habits as they are potentially at risk of developing a more severe form of the condition.

The invention claimed is:

1. An in vitro method for detecting a predisposition to a condition at least partially characterised by pathological or excessive formation of fibrotic tissue, the method comprising
   i) obtaining DNA comprising the Zf9 gene from a subject of interest, wherein said Zf9 gene comprises the sequence of SEQ ID NO:1 or the sequence of SEQ ID NO:2 and wherein nucleotide 43 of SEQ ID NO:1 and SEQ ID NO:2 is a polymorphic site,
   ii) amplifying a region of said Zf9 gene in said DNA comprising said polymorphic site, and
   iii) analyzing the amplification product resulting from step (ii) for the presence of guanosine at said polymorphic site,
   wherein the presence of guanosine at said polymorphic site indicates said subject is predisposed to said condition.

2. The method according to claim 1 wherein, in step (ii), a region comprising SEQ ID NO:1 is amplified.

3. The method according to claim 1 wherein the condition is Dupuytren's Disease.

4. A method according to claim 1 wherein the ZF9 gene, and regulatory elements thereof, is derived from a sample of genomic DNA.

5. A method according to claim 4 wherein the genomic DNA is isolated from blood or tissue samples.

6. A method according to claim 1 wherein, in step (ii), said region is amplified using polymerase chain reaction (PCR) primers.

7. A method according to claim 6 wherein said PCR primers are:

```
Forward primer:  5' GTCCAGGGTC ACCCACATAC 3'   (SEQ ID No. 3);

and

Reverse primer:  5' GTTCTGCACC CTACCCAGTT 3'   (SEQ ID No. 4).
```

8. A method according to claim 1 wherein said analyzing step (iii) is effected by restriction digestion and size analysis.

\* \* \* \* \*

SEQUENCE LISTING

<160> NUMBER OF SEQ ID NOS: 4

<210> SEQ ID NO 1
<211> LENGTH: 121
<212> TYPE: DNA
<213> ORGANISM: Artificial Sequence
<220> FEATURE:
<223> OTHER INFORMATION: Description of Artificial Sequence: primer

<400> SEQUENCE: 1
gtccagggtc acccacatac catgcaccac gggtgctatg ccgcttctta caggaccttt      60
ttagccctca aaagaccttc caaggagagg ccctggaggc aactgggtag ggtgcagaaa     120
c                                                                     121

<210> SEQ ID NO 2
<211> LENGTH: 121
<212> TYPE: DNA
<213> ORGANISM: Artificial Sequence
<220> FEATURE:
<223> OTHER INFORMATION: Description of Artificial Sequence: primer

<400> SEQUENCE: 2
gtccagggtc acccacatac catgcaccac gggtgctatg ccacttctta caggaccttt      60
ttagccctca aaagaccttc caaggagagg ccctggaggc aactgggtag ggtgcagaaa     120
c                                                                     121

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 3
gtccagggtc acccacatac                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
gttctgcacc ctacccagtt                                                  20